US00RE37919E

(19) United States
(12) Reissued Patent
Kronenberg et al.

(10) Patent Number: US RE37,919 E
(45) Date of Reissued Patent: Dec. 3, 2002

(54) RECOMBINANT DNA METHOD FOR PRODUCTION OF PARATHYROID HORMONE

(75) Inventors: Henry M. Kronenberg, Belmont, MA (US); Samuel R. Nussbaum, Weston, MA (US); Tomoko Doi, Nara (JP)

(73) Assignee: The General Hospital Corporation, Boston, MA (US)

(21) Appl. No.: 08/790,584

(22) Filed: Jan. 29, 1997

Related U.S. Patent Documents

Reissue of:
(64) Patent No.: 5,171,670
Issued: Dec. 15, 1992
Appl. No.: 07/350,979
Filed: May 12, 1989

U.S. Applications:
(

(63) Continuation of application No. 08/238,236, filed on May 4, 1994, now abandoned.

(51) Int. Cl.[7] ..... C12P 21/06; C12N 15/62; C12N 1/21; C07K 13/00

(52) U.S. Cl. ..... 435/68.1; 435/69.4; 435/69.7; 435/252.3; 435/252.33; 435/255.1; 435/320.1; 435/325; 530/350; 530/399; 536/23.1; 536/23.4; 536/23.51

(58) Field of Search ..... 435/68.1, 69.1, 435/69.4, 320.1, 252.3, 252.33, 246.2, 254.2; 530/300, 324, 350, 399

(56) References Cited

U.S. PATENT DOCUMENTS

| | | | | |
|---|---|---|---|---|
| 3,886,132 | A | 5/1975 | Brewer et al. | 260/112.5 |
| 4,366,246 | A | 12/1982 | Riggs | 435/68 |
| 5,208,041 | A | 5/1993 | Sindrey | 424/562 |
| 5,223,407 | A | 6/1993 | Wong et al. | 435/69.1 |

FOREIGN PATENT DOCUMENTS

| | | |
|---|---|---|
| EP | 0 176 341 | 4/1986 |
| EP | 0 293 249 | 11/1988 |
| EP | 0 336 324 | 10/1989 |
| EP | 0 357 391 | 3/1990 |
| WO | WO 88/03165 | 5/1988 |
| WO | WO 90/14415 | 11/1990 |

OTHER PUBLICATIONS

Partridge et al. 1980 FEBS Letters 115 (1) 139–142, Jan. 1980.*

Nishikawa, S., et al., "Efficient cleavage by α–thrombin of a recombinant fused protein which contains insulin–like growth factor I," *Protein Engineering* 1(6):487–492 (1987).

Statement from Opposition by Chugai Pharmaceutical Co. Ltd. in regards to Australian Patent Application 639,856 to Allelix Biopharmaceuticals Inc. and Glaxo Canada, Inc., Feb. 3, 1994.

Statement from Opposition by Chugai Pharmaceutical Co. Ltd. In regards to Australian Patent Application 639,856 to Allelix Biophaarmaceuticals Inc. and Glaxo Canada, Inc., Jul. 28, 1994.

Statutory Declaration of Thomas John Martin from Opposition by Chugai Pharmaceutical Co. Ltd. in regards to Australian Patent Application 639,856 to Allelix Biopharmaceuticals Inc. and Glaxo Canada, Inc., Aug. 2, 1994.

Statutory Declaration of Fiona Margaret Bathgate from Opposition by Chugai Pharmaceutical Co. Ltd. in regards to Australian Patent Application 639,856 to Allelix Biopharmaceuticals Inc. and Glaxo Canada, Inc., Jun. 23, 1994.

Statutory Declaration of Davin Merritt from Opposition by Chugai Pharmaceutical Co. Ltd. in regards to Australian Patent Application 639,856 to Allelix Biopharmaceuticals Inc. and Glaxo Canada, Inc., Aug. 3, 1994.

Statutory Declaration of Rodney Cruise from Opposition by Chugai Pharmaceutical Co. Ltd. in regards to Australian Patent Application 639,856 to Allelix Biopharmaceuticals Inc. and Glaxo Canada, Inc., Aug. 3, 1994.

Statutory Declaration of Debra Lee Tulloch from Opposition by Chugai Pharmaceutical Co. Ltd. in regards to Australian Patent Application 639,856 to allelix Biopharmaceuticals Inc. and Glaxo Canada, Inc., Aug. 29, 1994.

Statutory Declaration of Naoki Kubota from Opposition by Chugai Pharmaceutical Co. Ltd. in regards to Australian Patent Application 639,856 to Allelix Biopharmaceuticals Inc. and Glaxo Canada, Inc., Jul. 29, 1994.

Statutory Declaration of Naoki Kubota from Opposition by Chugai Pharmaceutical Co. Ltd. in regards to Australian Patent Application 639,856 to Allelix Biopharmaceuticals Inc. and Glaxo Canada, Inc., Aug. 29, 1994.

Declaration of Richard P. Bozzato from Response to Opposition by Chugai Pharmaceutical Co. Ltd. in regards to Australian Patent Application 639,856 to Allelix Biopharmaceuticals Inc. and Glaxo Canada, Inc., May 29, 1995.

Declaration of H. Scott Duncan from Response to Opposition by Chugai Pharmaceutical Co. Ltd. in regards to Australian Patent Application 639,856 to Allelix Biopharmaceuticals Inc. and Glaxo Canada, Inc., May 26, 1995.

Declaration of Dennis Sindrey from Response to Opposition by Chugai Pharmaceutical Co. Ltd. in regards to Australian Patent Application 639,856 to Allelix Biopharmaceuticals Inc. and Glaxo Canada, Inc., May 29, 1995.

Bachem Inc. 1993 Catalogue page describing PCAL175, human parathyroid hormone.

(List continued on next page.)

*Primary Examiner*—Marianne P. Allen
*Assistant Examiner*—Mary K. Zeman
(74) *Attorney, Agent, or Firm*—Sterne, Kessler, Goldstein & Fox PLLC

(57) ABSTRACT

A recombinant DNA molecule coding for human parathyroid hormone operably linked to an inducible bacterial promoter, a leader growth hormone sequence, and a selective enzymatic cleavage site, expression of the molecule in bacteria, and methods for producing large quantities of human parathyroid hormone and its variants.

30 Claims, 6 Drawing Sheets

OTHER PUBLICATIONS

Barling and Lowe, "The biological properties of bovine parathyroid hormone (1–41), a fragment generated from the native hormone by human leukocytes", *Bioscience Reports* 7(1):43–50 (1987).

Born et al., "Comparison of biological and biochemical properties of a PTH–inhibitor in pseudohypoparathyroidism type I and of human PTH (3–84) synthesized in *E. coli*", Chemical Abstracts, 107:419, Abstract No. 215673K (1987).

Born et al., "Human Preproparathyroid Hormone Synthesized in *Escherichia coli* is transported to the Surface of the Bacterial Inner Membrane but Not Processed to the Mature Hormone", *Mol. Endo.* 1:5–14 (1987).

Born et al., "Inhibition of parathyroid hormone bioactivity by human parathyroid hormone (PTH)–(3–84) and PTH–(8–84) synthesized in *Escherichia coli", Endocrinology* 123(4):1848–1853 (1988).

Bovine Parathyroid Hormone (1–84) Material Safety Data Sheet, Bachem. Inc. Fine Chemicals, date signed Feb. 6, 1983.

Bovine Parathyroid Hormone Certificate of Analysis, HPLC dated Nov. 12, 1992.

Breyel et al., "Synthesis of Mature Human Parathyroid Hormone in *Escherichia coli", 3rd Europ. Cong. Biotech.* 3:363–369 (1984).

Caporale and Rosenblatt, "Parathyroid hormone antagonists effective in vivo", *Adv. Exp. Med. Biol.* 208:315–327(1986).

Caulfield et al., "A chemically synthesized radiolabeled signal peptide: Design, preparation, and biological evaluation of an iodinated analog of preproparathyroid hormone", *Mol. Endo.* 2(5):452–458 (1988).

Caulfield et al., "Correlation of secondary structure with biological activity for a leader peptide: Circular dichroism–derived structure and in vitro biological activities of preproparathyroid hormone peptide and its analogs", *Arch Biochem. Biophys.* 289(2):208–213 (Sep. 1988).

Demay et al., "Comparison of renal and osseous binding of parathyroid hormone and hormonal fragments", *Am. J. Physiol.* 249:E437–E446 (1985).

Duong et al., "Synthetic signal peptide and analogs display different activities in mammalian and plant in Vitro secretion systems", *J. Biol. Chem.* 262(13):6328–6333 (May 5, 1987).

Dykes et al., "Expression of atrial natriuretic factor as a cleavable fusion protein with chloramphenicol acetyltransferase in *Escherichia coli", Eur. J. Biochem.* 174:411–416 (1988).

Fairwell et al., "Total solid–phase synthesis, purification, and characterization of human parathyroid hormone–(1–84)", *Biochem.* 22(11):2691–2697 (1983).

Freeman et al., "Consequences of amino–terminal deletions of preproparathyroid hormone signal sequence", *Molecular Endocrinology* 1(9):628–638 (1987).

Germino et al., "Rapid purification of a cloned gene product by genetic fusion and site–specific proteolysis", *Proc. Natl Acad. Sci. USA* 81: 4692–4696 (Aug. 1984).

Goldman et al., "A new highly potent parathyroid hormone antagonist: [D–TRP$^{12}$, TYR$^{34}$]bPTH–(7—34)$NH_2$", *Endocrinology* 123(5):2597–2599 (1988).

Goldman et al., "Evaluation of novel parathyroid hormone analogs using a bovine renal membrane receptor binding assay", *Endocrinology* 123(3):1468–1475 (1988).

Goud et al., Solid–Phase Synthesis and Biological Activity of Human Parathyroid Hormone (1–84), draft manuscript.

Gutierrez et al., "Inhibition of parathyroid hormone–responsive adenylate cyclase in clonal osteoblast–like cells by transforming growth factor α and epidermal growth factor", *J. of Biological Chemistry* 262(33):15845–15850 (Nov. 25, 1987).

Hoeger et al., "Preparative reversed phase high performance liquid chromatography: Effects of buffer pH on the purification of synthetic peptides", *Biochromatography* 2(3):134–142 (1987).

Horiuchi and Rosenblatt, "Evaluation of a parathyroid hormone antagonist in an in vivo multiparameter bioassay", *Am. J. Physiol.* 253:E187–E192 (1987).

Ikehara et al., "Synthesis of a gene for human growth hormone and its expression in *Escherichia coli", Proc. Natl. Acad. Sci. USA* 81:5956–5960 (Oct. 1984).

Itakura et al., "Expression in *Escherichia coli* of a Chemically Synthesized Gene for the Hormone Somatostatin", *Science* 198:1056–1063 (Dec. 9, 1977).

Kemp et al., "Parathyoid hormone–related protein of malignancy: Active synthetic fragments", *Science* 238:1568–1570 (Dec. 11, 1987).

Kimura et al., "Solution synthesis of [ASN$^{76}$]–human parathyroid hormone(1–84)", *Biochem. Biophys. Research Commun.* 114(2):493–499 (Jul. 29, 1983).

Kimura et al., "Total synthesis of human parathyroid hormone (1–84)", *J. Chem. Soc., Chem. Commu.,* pp. 340–341 (1982).

Knott et al., "The isolation and characterisation of human atrial natriuretic factor produced as a fusion protein in *Escherichia coli", Eur. J. Biochem.* 174:405–410 (1988).

Kronenberg, H.M., "Expression of the human parathyroid hormone gene", *Biomedical Science: Current Research on Calcium–Regulation Hormones*, The University of Texas Medical Branch Series, Cooper, C.W. (Ed.), University of Texas Press, Austin, Texas, pp. 1–6 (1987).

Kumagaye et al., "Comparision of reversed–phase and cation–exchange high–performance liguid chromatography for separating closely related peptides: Separation of ASP$^{76}$–human parathyroid hormone (1–84) from ASN$^{76}$–human parathyroid hormone (1–84)", *J. oc Chromatography* 327:327–332 (1985).

McKee et al. "The 7–34–fragment of human hypercalcemia facrot is a partial agonist/antagonist for parathyroid hormone–stimulated cAMP production", *Endocrinology* 122(6):3008–3010 (1988).

Mitchell et al., "Biochemical and morphological characterization of parathyroid hormone receptor binding to the rat osteosarcoma cell line UMR–106", *Endocrinology* 126(5):2327–2335 (1990).

Morelle & Mayer, "Increased synthesis of human parathyroid hormone in *Escherichia coli* through alterations of the 5' untranslated region", *Biochim. et Biophys. Acta* 950:459–462 (1988).

Moseley et al., "Parathyroid hormone–related protein purified from a human lung cancer cell line", *Proc. Natl. Acad. Sci. USA* 84:5048–5052 (Jul. 1987).

Nagai & Thogersen, "Generation of β–globin by sequence–specific proteolysis of a hybrid protein produced in *Escherichia coli", Nature* 309:810–812 (Jun. 28, 1984).

Nissenson et al., "Activation of the parathyroid hormone receptor–adenylate cyclase system in osteosarcoma cells by a human renal carcinoma factor", *Cancer Research* 45:5358–5363 (Nov. 1985).

Nissenson et al., "Synthetic peptides comprising the amino–terminal sequence of a parathyroid hormone–like protein from human malignancies", *J. of Biological Chemistry* 263(26):12866–12871 (Sep. 15, 1988).
Pun, K.K., "The importance of parathyroid hormone in inhibition of collagen syntheses and mitogenesis of osteoblastic cell", *J. Biochem.* 106:1090–1093 (1989).
Rabbani et al., "Influence of the amino–terminus on in vitro and in vivo biological activity of synthetic parathyroid hormone–like peptides of malignancy", *Endocrinology* 123(6):2709–2716 (1988).
Rabbani et al., "Purification of peptides with parathyroid hormone–like bioactivity from human and rat malignancies associated with hypercalcemia", *Endocrinology* 118(3):1200–1210 (1986).
Rabbani et al., "Recombinant human parathyroid hormone synthesized in *Eschericia coli", J. of Biol. Chem.* 263(3):1307–1313 (Jan. 25, 1988).
Rizzoli & Bonjour, "Effects of lectins and tunicamycin on cAMP response to parathyroid hormone", *Am. J. Physiol.* 256:E80–E86 (1989).
Rodan et al., "Comparison of postreceptor effects of 1–34 human hypercalcemia factor and 1–34 human, parathyroid hormone in rat osteosarcoma cells", *J. Clin. Invest.* 81:924–927 (Mar. 1988).
Rosenblatt et al., "A tumor–secreted protein associated with human hypercalcemia of malignancy", *Ann N.Y. Acad. Sci.* 548:137–145 (1988).
Scholtissek & Grosse, "A plasmid vector system for the expression of a triprotein consisting of β–galactosidase, a collagenase recognition site and a foreign gene product", *Gene* 62:55–64 (1988).
Selz et al., "Regulation of Na–dependent $P_i$ transport by parathyroid hormone in osteoblast–like cells", *Am. J. Physiol.* 256 (Endocrinol. Metabl. 19) :E93–E100, (1989).
Smith & Johnson, "Single–step purification of polypeptides expressed in *Escherichia coli* as fusions with glutathione S–transferase", *Gene* 67:31–40 (1988).
Strewler et al., "Parathyroid hormonelike protein from human renal carcinoma cells", *J. Clin. Invest.* 80:1803–1807 (Dec. 1987).
Suva et al., "A parathyroid hormone–related protein implicated in malignant hypercalcemia: Cloning and expression", *Science* 237:893–896 (Aug. 21, 1987).
Thiede et al., "Human renal carcinoma expresses two messages encoding a parathyroid hormone–like peptide: Evidence for the alternative splicing of a single–copy gene", *Proc. Natl. Acad. Sci. USA* 85:4605–4609 (Jul. 1988).
Thompson et al., "Direct action of the parathyroid hormone–like human hypercalcemic factor on bone", *Proc. Natl. Acad. Sci. USA* 85:5673–5677 (Aug. 1988).
Tosteson et al., "The synthetic precursor specific region of pre–pro–parathyroid hormone forms ion channels in lipid billayers", *Biosci, Rep.* 8(2):173–183 (1988).
Vasicek et al., "Nucleotide sequence of the human parathyroid hormone gene", *Proc. Natl. Acad. Sci. USA* 80:2127–2131 (Apr. 1983).
Wingender et al., "Expression of human parathyroid hormone in *Escherichia coli", J. of Biol. Chem.* 264(8):4367–4373 (Mar. 15, 1989).
Yasukawa et al., "Production of human B cell stimulatory factor–2 (BSF–2/IL–6) using a genetic engineering technique", Chemical Abstracts 110:171, Abstract No. 226531a (1989).
Yasukawa et al., "Production of human B cell stimulatory factor–2 (BSF–2/IL–6) using a genetic engineering technique", *J. of TOSHO Research* 32(2):161–168 (1988).
Chicz, R.M. et al. 1990 Methods in Enzymology vol. 182 pp. 392–421.*

* cited by examiner

RECOMBINANT DNA METHOD FOR PRODUCTION OF PARATHYROID HORMONE

Matter enclosed in heavy brackets [ ] appears in the original patent but forms no part of this reissue specification; matter printed in italics indicates the additions made by reissue.

*This application is a continuation of application Ser. No. 08/238,236, filed May 4, 1994, abandoned, which is a Reissue of application Ser. No. 07/350,979, filed May 12, 1989, U.S. Pat. No. 5,171,670.*

BACKGROUND OF THE INVENTION

1. Field of the Invention

The invention relates to a method for producing large quantities of human parathyroid hormone 1–84 (hPTH 1–84) or variants thereof in bacteria using recombinant DNA techniques.

2. Description of the Background Art

Parathyroid hormone (PTH) is an 84-amino acid residue peptide and one of the main regulators of calcium homeostasis in the mammalian organism. PTH acts primarily on the kidney, stimulating calcium resorption, and on bone cells, stimulating calcium mobilization. PTH also leads to enhancement of the bone remodeling process (sec Potts et al. *Adv. Protein Chem.* 32:323–395 (1982)). PTH may have promising effects in the therapy or prevention of osteoporosis.

Variants or analogs of PTH can bind to PTH receptors and block the effects of either PTH, or of the recently discovered PTH-Rotated Peptide, which is produced by a number of tumors such as renal cell carcinoma and carcinomas of the lung and breast, and is now thought to be responsible for hypercalcemia of malignancy (Broadus, A. et al., *New. Eng. J. Med.* 319:356–363 (1988)).

For the foregoing reasons, a source of large quantities of easily purified human PTH has been sought for a number of years.

Several reports have described direct expression of PTH, in *E. coli* (Breyel et al., *3rd Europ. Cong. Biotech.* 3:363–369 (1984); Born, W. et al., *Endocrinol.* 123:1848–1853 (1988); Morelle, et al., *Biochim. Biophys. Acta* 950 459–462 (1988); Rabbani et al. *J. Biol. Chem.* 263:1307–1313 (1988)). The attempts of Breyel et al. and Morelle et al. (supra) to express human PTH yielded only very limited amounts of hormone (<500 μg/liter) due to RNA and protein instability. Rabbani et al. (supra) achieved yields of 200 μg liter PTH, which was contaminated with peptides variously truncated at the N-terminus. Once the pure intact PTH(1–84) was purified by an intricate method, the final yield was only 10 μg/liter culture. Born et al. (supra), using a multicopy plasmid of human preproPTH cDNA, achieved expression of truncated hPTH, largely the PTH(3–84) and PTH(8–84), which were virtually devoid of PTH bioactivity.

Thus, the need was recognized for an expression vector which would lead to production of higher quantities of stable PTH, that could be easily purified, and was devoid of inactive forms/analogs of PTH. One approach to the solution of this problem was suggested by work describing expression of other peptides in bacterial hosts (Itakura et al., *Science* 198:1036–1063 (1977); Riggs, U.S. Pat. No. 4,366,246, Method for Microbial Polypeptide Expression, (Dec. 28, 1982); Ikehara et el., *Proc. Natl. Acad. Sci. USA* 81:3956–5960 (1984)).

Itakura et al. (1977, supra) and Riggs (1984, supra) taught methods for bacterial expression of a foreign protein, specifically the production of a fusion protein between a desired heterologous protein (human somatostatin) and a large bacterial protein (betagalactosidase). The fusion protein served the function of preventing intracellular degradation of the foreign protein. Furthermore, overexpressed fusion proteins, especially with β-galactosidase, are frequently deposited as inclusion bodies in the bacterial cells, and are therefore easier to isolate and purify (Marston, *Biochem. J.* 240:1–12 (1986)). The somatostatin gene was inserted in phase at the C-terminus of the β-galactosidase gene, and the presence of a methionine at the N-terminus of the somatostatin sequence was put in to allow later cleavage of the fusion protein by cyanogen bromide. An inducible bacterial promoter, the lac promoter was inserted to stimulate transcription of the fusion protein mRNA. Amino acid codons known to be favored in *E. coli* for the production of non-bacterial proteins (e.g. MS2 phage) were utilized. The fusion protein was solubilized with 70% formic acid, 6M guanidinium HCl, 8M urea, or 2% SDS, and the desired product, somatostatin, was subsequently enriched using CNBr cleavage, alcohol extraction, and chromatography. Suggestion was made to alternate cleavage methods based on the concept of selective cleavage sites: Just as methionine could be inserted at the desired junction to serve as a target site for cyanogen bromide, so too could specific amino acid sites be introduced which could be attacked by proteolytic enzymes with amino acid specificity.

Ikehara et al. (1984, supra) described a plasmid containing the *E. coli trp* promoter which promotes the expression of a synthetic human gene for growth hormone (hGH), leading to enhanced synthesis of the 191 amino acid (hGH), peptide. The synthetic gene utilized amino acid colons most frequent in *E coli.*

Nagai et al. (*Nature* 309:810–812 (1984) pointed out the limitations on high level expression of eukaryotic genes in *E. coli*, even when appropriate promoters and ribosomal binding sequences have been introduced, and disclosed the production of the desired gene product in a fusion protein as a useful method to increase efficiency easy separation of the desired peptide. To achieve this goal, Nagai et al. introduced a sequence of 4 amino acids which serve as a cleavage site for the blood coagulation factor Xa, and achieved expression of the human beta globin gene fused to part of the phage lambda cII gene. Cleavage by Factor Xa eliminated the extra N-terminal methionine encoded by the initiation colon which is present in most eukaryotic proteins expressed in *E. coli* by conventional methods.

Other documents describe the design and use of plasmids coding for fusion proteins between a desired heterologous protein and a second protein, some of which include cleavage sites recognized by Factor Xa or thrombin, for enhanced expression in bacteria and greater ease of purification of the desired protein (Germino et al., *Proc. Natl. Acad. Sci. USA* 81:692–4696 (1984); Scholtissek et al., *Gene* 62:55–64 (1988);Smith et al., *Gene* 67:31–40 (1988); Knott et al., *Eur. J. Biochem.* 174:403–410 (1988); and Dykes et al., *Eur. J. Biochem.* 174:411–416 (1988)).

Wingender et al., *J. Biol. Chem.* 264:4367–4373 (1989)) attempted to apply the above-mentioned approaches in order to achieve enhanced expression of hPTH in *E. coli*. Attempts to introduce the factor Xa recognition site into an expression plasmid, upstream from the hPTH site, as described by Nagai et al. (1985, supra) and to achieve isolation of hPTH from the fusion protein using proteolytic cleavage with factor Xa were unsuccessful, even when highly purified fusion protein and proteinase were used.

BRIEF SUMMARY OF THE INVENTION

The availability of hPTH and analogs which are selectively antagonists and can block the untoward effects mediated by agonists acting at PTH receptors in certain pathologic states would be of great clinical value. For this purpose, a prokaryotic expression system would be of great utility. Such a system would provide not only sufficient material for clinical and research use, but also would allow application of protein engineering methods to investigate structure-function relationships and to design hormone variants to perform specific tasks (e.g. calcium mobilization vs. bone reconstruction, agonistic vs. antagonistic effects).

This invention pertains to a recombinant DNA molecule coding for human parathyroid hormone capable of being expressed efficiently in bacteria. The DNA molecule comprises a control region for expression of a genetic sequence in a host, said region being in operable linkage with a leader sequence coding for a polypeptide sequence, said leader sequence being no more than about 600 nucleotides in length, and being operably linked to a nucleotide sequence coding for a selective enzymatic cleavage site, said nucleotide sequence being linked to and preceding said genetic sequence to be expressed.

The invention is additionally directed to a fusion protein comprising a leader polypeptide, a selected enzymatic cleavage site, and hPTH(1–84) or its variants.

The invention also includes a method for producing large quantities of human parathyroid hormone 1–84 (hPTH 1–84), or variants thereof, in bacteria using the said recombinant DNA molecule.

One of the major advantages of this invention is the ability to produce high concentrations of purified hPTH 1–84, which is a 50–100 fold improvement over currently attainable levels.

The invention enables production of a stable form of hPTH 1–84 resistant to bacterial intracellular degradation, which lacks the added N-terminal methionine which, if present, would render the hormone preparation less active and more immunogenic to a human host.

The invention also permits one to tailor the plasmid construct for production of hPTH analogues with variant N-termini which could serve as useful parathyroid hormone agonists or antagonists.

DESCRIPTION OF THE PREFERRED EMBODIMENTS

Human parathyroid hormone (hPTH) is a polypeptide of 84 amino acid residues (hPTH(1–84)). Its amino acid sequence (Keutmann, H. T. et al., *Biochemistry* 17:5723–5729 (1978)) and the nucleotide sequence of the gene coding for it (Handy et al. *Proc. Natl Acad. Sci. USA* 78;7365–7364 (1981)) are known.

Figure 2:
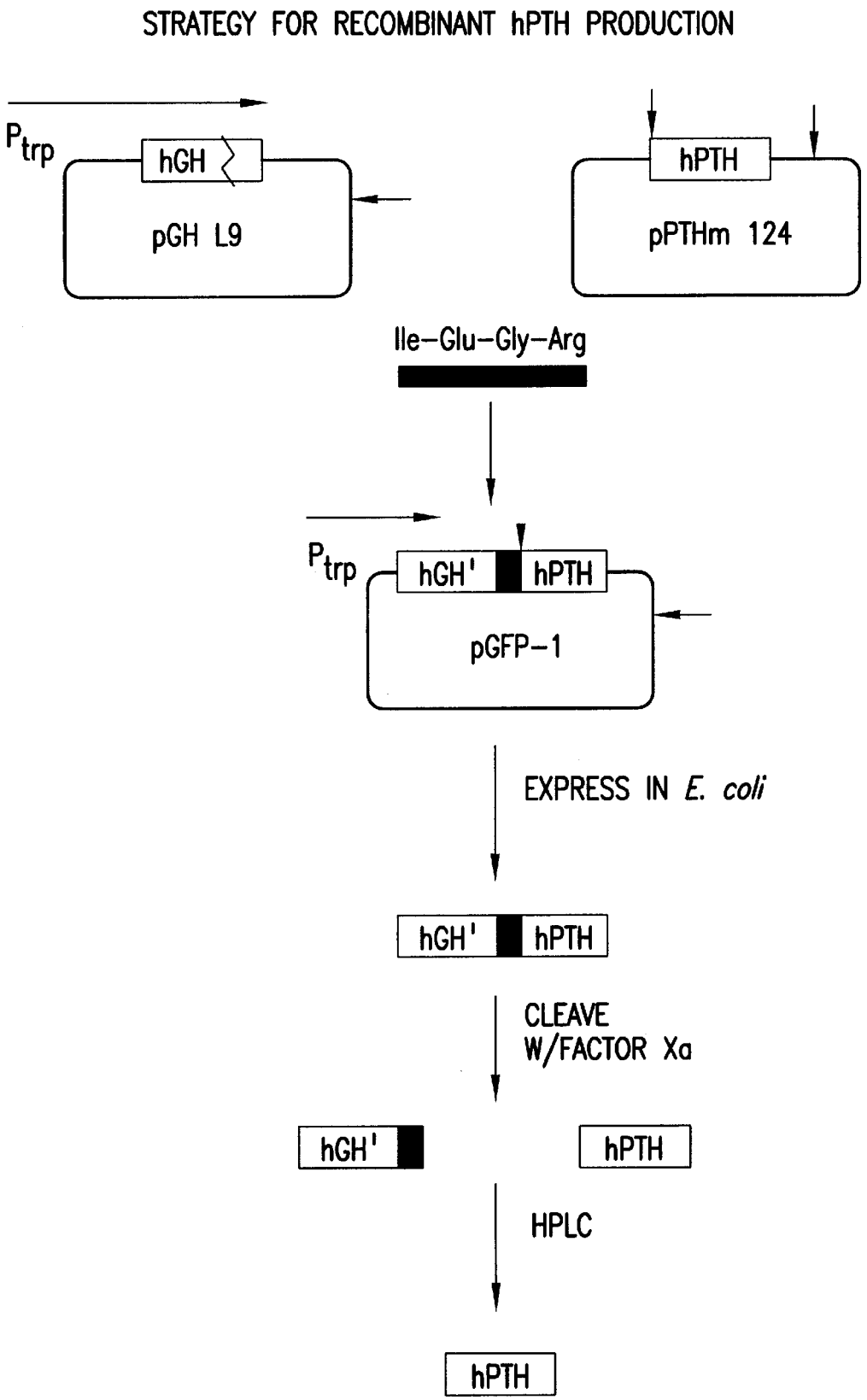
FIG. 2 shows schematically the strategy for recombinant hPTH production. The starting plasmid, pGH-L9, contains an *E. coli* tryptophan promoter and a nucleotide sequence coding for human GH which contains BglII and SalI restriction sites. The 35 nucleotide oligomer carrying the FXRS (see FIG. 1) was cloned into pGH-L9 at a BglII-SalI site. The resultant intermediate plasmid (pTGI, not shown), thus contained nucleotides coding for amino acids 1–138 of human GH linked to the FXRS sequence. This intermediate plasmid was treated with StuI to create a blunt end 3' from the codon coding for Arg. The genetic sequence coding for hPTH was cut from the pPTHm124 plasmid with XbaI, blunt ended, and the XbaI site filled using the Klenow reagent, and the resultant sequence cloned into the pTGI intermediate plasmid. This procedure allowed the N-terminal codon of hPTH to abut the Arg codon of the FXRS fragment. This newly constructed plasmid was termed pGFP-1. The plasmid was subsequently expressed in *E. coli*, which produced the fusion protein containing hGH (1–138), the FXRS, and the hPTH(1–84) sequences. Cleavage with factor Xa released the intact hPTH(1–84) hormone in which the N-terminal serine residue was unmodified. The hPTH was then purified by HPLC.

The hPTH(1–84) nucleotide sequence can be obtained from a number of known sources. For example, the plasmid pPTHm124 (Born et al., *Molec. Endocrinol.* 1:5–14 (1987)) contains the sequence, and served as the source for the DNA used to construct the pGFP-1 plasmid of this invention (see FIG. 2).

The biological activities of hPTH, and methods for assaying these activities, are well known in the art (See, for example, Potts et al. *Adv. Protein Chem.* 32:323–395 (1982)). These activities include binding to receptors on kidney cells and on various tumor cell lines, and the stimulation of cyclic AMP production.

As used herein, a "variant" of hPTH is a polypeptide which possesses biological activity that is substantially similar to a biological activity hPTH. Such biological activity includes the binding to a receptor for hPTH and preventing the subsequent binding or action of hPTH at that receptor. A molecule is said to be "substantially similar" to another molecule if both molecules have substantially similar structures or if both molecules possess a similar biological activity. The "variants" of recombinant hPTH include both "fragments" and "variants" of recombinant hPTH.

The term "fragment of hPTH" is meant to refer to any polypeptide subset of that molecule. The term "variant of hPTH" is meant to refer to a molecule substantially similar in structure to either the entire molecule, or to a fragment thereof provided that the "variant" has at least one biological activity that is either similar to a biological activity of hPTH. Thus, provided that a molecule possesses at least one biological activity that is similar to an activity of hPTH (including the binding to a hPTH receptor and inhibiting the subsequent binding of hPTH), it is considered a "variant" of hPTH as that term is used herein, even if one of the molecules contains one or more amino acids not found in the other, or if the sequences of amino acid residues in the two molecules are not identical.

As contemplated in this invention, any variant of hPTH may be expressed and produced as long as it retains hPTH bioactivity, including the capacity to bind to hPTH receptors and function as a hPTH antagonist, Variants of hPTH are produced by recombinant means. Truncated variants are produced by synthesizing polynucleotide expressible as polypeptides, that are missing amino acid residues from one or the other terminus.

The synthetic analog of bovine PTH, PTH (3–34) has been recognized as a potent PTH antagonist in vitro. Variants of hPTH lacking N-terminal amino acids 1–2 and 1–7, were shown to be devoid of agonist activity and capable of antagonist activity (Born, W. et. al., *Endocrinol.* 23:1848–1853 (1988)). Preferred variants of hPTH of this invention are variants truncated at the N-terminus. When a variant is truncated by one amino acid at the N -terminus, it is termed hPTH(2–84), in that it lacks residue #1 but contains residues #2–84. Likewise, variants truncated at the N-terminus are termed hPTH(3–84), hPTH(4–54), etc. The preferred variants of this invention are hPTH(384), (4–84), (5–84), (6–84), (7–84), and (8–84).

By the term "fusion protein" is intended a fused protein comprising human PTH, or a variant thereof, linked at its N-terminus to a "selective cleavage site," which is in turn, linked at its N-terminus to an additional amino acid leader polypeptide sequence. The linkage in the fusion protein is via conventional peptide bonds, produced in the host cell during protein biosynthesis, from the mRNA transcribed from the genetic sequences which comprises part of this invention.

The term "selective cleavage site" refers to an amino acid residue or residues which can be selectively cleaved with either chemicals or enzymes and where cleavage can be achieved in a predictable manner. A selective enzymatic cleavage site is an amino acid or a peptide sequence which is recognized and hydrolyzed by a proteolytic enzyme. Examples of such sites include trypsin or chymotrypsin cleavage sites. In a preferred embodiment of this invention, the selective cleavage site is comprised of the sequence Ile-Glu-Gly-Arg, which is recognized sad cleaved by blood coagulation factor Xa. In another embodiment, the selective cleavage site has the sequence Leu-Val-Pro-Arg, which is recognized and cleaved by thrombin.

Figure 1A:
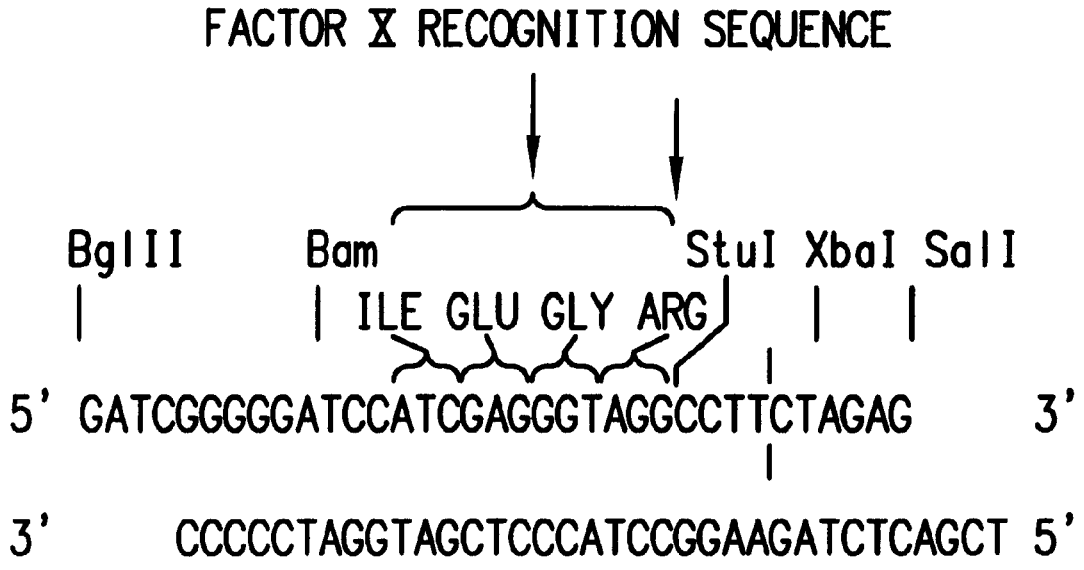
FIG. 1 shows the oligonucleotide fragment containing the factor Xa recognition sequence (FXRS) and an analogous fragment containing the thrombin recognition sequence, indicating the presence of restriction sites. Of particular importance is the StuI site 3' to the Arg codon, which allows joining with the 5' terminus of the hPTH coding sequence.
Figure 1B:
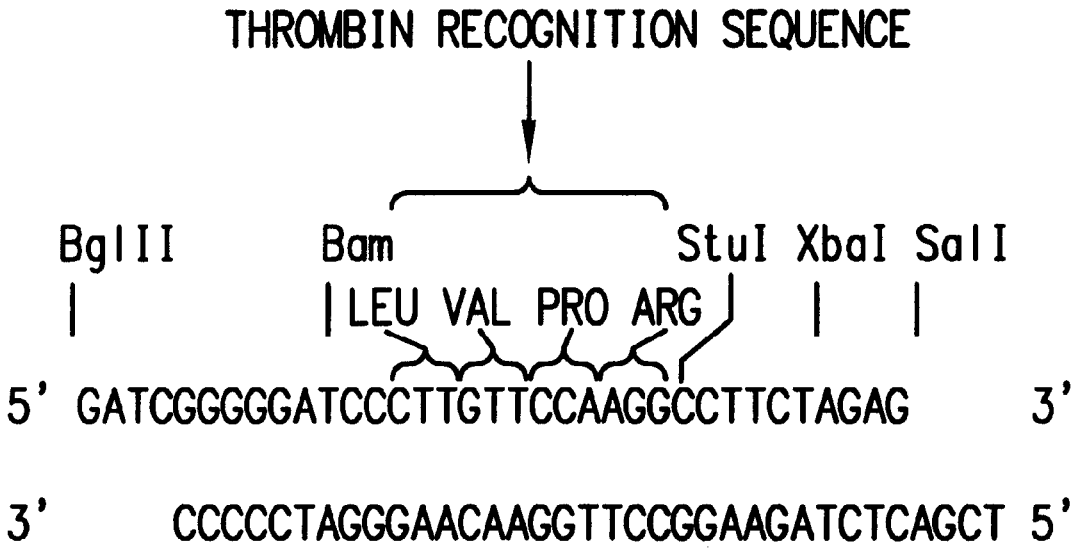

The size of the oligonucleotide sequence 5' to the sequence coding for the enzyme recognition site can vary. In a preferred embodiment 13 nucleotides are situated between the codon for Ile (the start of the recognition site) and the 3' end of the leader sequence. In other embodiments longer sequences can be used. These upstream sequences must contain appropriate restriction sites to allow them to be cloned into the DNA adjacent to the leader sequence, as is the case for the BglII site of the oligonucleotide containing the Factor X recognition site (FXRS) (see FIGS. 1 and 2).

By the term "leader sequence" is intended a polynucleotide sequence linked to the hPTH, and expressed in host cells as n fusion protein fused to the selective cleavage site and the hPTH. The term "leader polypeptide" describes the expressed form of the "leader sequence" as obtained in the fusion protein.

In one embodiment, a leader sequence of no more than about 600 nucleotides is utilized. In another embodiment, a nucleotide sequence coding for human growth hormone (191 amino acid residues) is used, resulting in a fusion protein in which the leader polypeptide is human growth hormone (Ikehara et al., *Proc. Natl. Acad. Sci. USA* 81:5956–5960 (1984)). In another embodiment, the leader polypeptide is composed of about 50 amino acids. In yet another embodiment, the leader polypeptide is composed of about 100 amino acids.

The leader sequence as used in this invention can be less that the number of nucleotides required to code for a complete human growth hormone polypeptide, and can therefore code for a shortened variant of human growth hormone, as expressed in the fusion protein. In a preferred embodiment, the leader sequence comprises a nucleotide sequence coding for residues 1–138 of human growth hormone.

The fusion protein, which is often insoluble and found in inclusion bodies when it is overexpressed, is purified from other bacterial proteins by methods well known in the art. In a preferred embodiment, the insoluble fusion proton is centrifuged and washed after cell lysis, resolubilized with guanidine-HCl. It can remain soluble after removal of the denaturant by dialysis. (For purification of retractile proteins, sec Jones, U.S. Pat. No. 4,512,922; Olson, U.S. Pat. No. 4,518,526; Builder et al., U.S. Pat. Nos. 4,511,502 and 4,620,948.

The recombinant hPTH can be purified to be substantially free of natural contaminants from the solubilized fusion protein through the use of any of a variety of methodologies. As used herein, a compound is said to be "substantially free of natural contaminants" if it has been substantially purified from materials with which it is found following expression in bacterial or eukaryotic host cells. The hPTH may be purified through application of standard chromatographic separation technology.

Alternatively, the peptide may be purified using immunoaffinity chromatography (Rotman, A., et al., *Biochim. Biophys. Acta* 641:114–121 (1481); Sairam, M. R., *J. Chromatog* 215:143–152 (1981); Nielsen, L. S., et al., Biochemistry 21:6410–6415 (1982); Vockley, J., et al., *Biochem. J.* 217:535–542 (1984); Paucha, E., et al. *J. Virol.* 51:670–681 (1984); Chong, P., et al., *J. Virol. Meth.* 10:261–268 (1985)).

After partial or substantial purification, the fusion protein is treated enzymatically with the enzyme corresponding to the selective cleavage site. Alternatively, the fusion protein in its more impure state, even in refractile form, can be treated with the enzyme. If needed, the resulting mature hPTH, or variant thereof, can be further purified.

Conditions for enzymatic treatment are known to those of skill in the art.

The expression of a DNA sequence requires that the DNA sequence be "operably linked" to DNA sequences which contain transcriptional sad translational regulatory information. An operable linkage is a linkage in which the control or regulatory DNA sequences and the DNA sequence sought to be expressed are connected in such a way as to permit gent; expression. The precise nature of the "control regions" needed for gene expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. Regulatory regions in eukaryotic cells will in general include a promoter region sufficient to direct the initiation of RNA synthesis.

Two DNA sequences are said to be operably linked if the nature of the linkage between the two DNA sequences does not (1) result in the introduction of a frame-shift mutation, (2) interfere with the ability of the promoter region sequence to direct the transcription of the fusion protein-encoding sequence or (3) interfere with the ability of the fusion protein-encoding sequence to be transcribed by the promoter region sequence. Thus, a promoter region would be operably linked to a DNA sequence if the promoter were capable of transcribing that DNA sequences.

To express the hPTH molecule (or a variant or functional derivative thereof) in a prokaryotic cell (such as, for example, *E. coli. B. subtilis. Pseudomonas. Streotomyces*, etc.), it is necessary to operably link the hPTH-encoding sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene of pBR322, and the CAT promoter of the chloramphenicol acetyl transferase gene of pPR325, etc. Examples of inducible prokaryotic promoters include the major right and left promoters of bacteriophage λ ($P_L$ and $P_R$), the *trp, recA, lacZ, lacI.* and *gal* promoters of *E. coli.* the α-amylase (Ulmanen, I., et al., *J. Bacterial.* 162:176–182 (1985)) and the σ-28-specific promoters of *B. subtilis* (Gilman, M. Z., et al., *Gene* 32:11–20 (1984)), the promoters of the bacteriophages of *Bacillus* (Gryczan, T. J., In: *The Molecular Biology of the Bacilli*, Academic Press, Inc., NY (1982)), and Streotomyces promoters (Ward, J. M., et al., *Mol. Gen. Genet.* 203:468–478 (1986)). Prokaryotic promoters are reviewed by Glick, B. R., (*J. Ind. Microbiol.* 1:277–282 (1987)); Cenatiempo, Y. (*Biochimie* 68:505–516 (1986)); and Gottesman, S. (*Ann. Rev. Genet.* 18:415–442 (1984)).

The joining of various DNA fragments, to produce the expression vectors of this invention is performed in accordance with conventional techniques, employing blunt-ended or staggered-ended termini for ligation, restriction enzyme digestion to provide appropriate termini, filling in of cohesive ends as appropriate, alkali and phosphatase treatment to avoid undesirable joining, and ligation with appropriate ligases. The genetic construct encodes an inducible promoter which is operably linked to the 5' gene sequence of the fusion protein, to allow efficient expression of the fusion protein.

The preferred prokaryotic promoter for this invention is the *E. coli trp* promoter, which is inducible with indole acrylic acid.

Proper expression in a prokaryotic cell requires the presence of a ribosome binding site upstream of the gene-encoding sequence. Such ribosome binding sites are disclosed, for example, by Gold, L., et al. (*Ann. Rev Microbiol.* 35:365–404 (1981)).

If expression is desired in a eukaryotic cell, such as yeast, fungi, mammalian cells, or plant cells, then it is necessary to employ a promoter capable of directing transcription in such a eukaryotic host. Preferred eukaryotic promoters include the promoter of the mouse metallothionein I gene (Homer, D., et al., *J. Mol. Appl. Gen.* 1:273–288 (1982)); the TK promoter of Herpes virus (McKnight, S., *Cell* 31:355–365 (1982)); the SV40 early promoter (Benoist, C., et al., *Nature* (*London*) 290:304–310 (1981)); and the yeast *ga*14 gene promoter (Johnston, S. A., et al., *Proc. NatlAcad. Sci.* (*USA*) 79:6971–6975 (1982); Silver, P. A., et al., *Proc. Natl. Acad. Sci.* (*USA*) 81:5931–5955 (1984)).

Preferably, the introduced pane sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli* (such as; for example, pBR322, ColEl, pSC101, pACYC 184, π VX. Such plasmids are, for example, disclosed by Maniatis, T., et al. (In: *Molecular Cloning, A Laboratory Manual*, Cold Spring Harbor Press, Cold Spring Harbor, N.Y. (1982)). *Bacillus* plasmids include pC194, pC221, pT127, etc. Such plasmids are disclosed by Gryczan, T. (In: *The Molecular Biology of the Bacilli*, Academic Press, NY (*1982*), pp. 307–329). Suitable *Streptomyces* plasmids include pIJIOI (Kendall, K. J., et al., *J. Bacterial.* 169:4177–4183 (1987)), and streptomycin bacteriophages such as φC31 (Chester, K. F., et al., In: *Sixth International Symposium on Actinomycetales Biology*, Akademiai Kaido, Budapest, Hungary (1986), pp. 45–54). *Pseudomonas* plasmids are reviewed by John, J. F., et al. (*Rev. Infect. Dis.* 8:693–704 (1986)), and Izaki, K. (*Jon. J. Bacterial.* 33:729–742 (1978)).

Preferred eukaryotic plasmids include BPV, vaccinia, SV40, 2-micron circle, etc. Such plasmids are well known in the art (Holstein, D., et al., *Miami Wntr. Symp.* 19:265–274 (1982); Broach, J. R., In: *The Molecular Biology of the Yeast Saccharomyces: Life Cycle and Inheritance*, Cold Spring Harbor Laboratory, Cold Spring Harbor, N.Y., p. 445–470 (1981); Broach, J. R., *Cell* 28:203–204 (1982); Bollon, D. P., et al., *J. Clin. Hematol. Oncol.* 10:39–48 (1980); Maniatis, T., In: *Cell Biology: A Comprehensive Treatise. Vol.* 3, *Gene Expression, Academic Press, N.Y., pp.* 563–608 (1980)).

The preferred bacterial host for this invention is *E. coli*. In other embodiments, other bacterial species can be used. In yet other embodiments, eukaryotic cells may be utilized, such as, for example, yeast, filamentous fungi, or the like. Use of these cell types are well known in the art. Any host tray be used to express the protein which is compatible with replicon and control sequences in the expression plasmid. In general, vectors containing replicon and control sequences are derived from species compatible with a host cell are used is connection with the host. The vector ordinarily carries a replicon site, as well as specific genes which are capable of providing phenotypic selection in infected or in transformed cells. The expression of the fusion protein can also be placed under control with other regulatory sequences which may be homologous to the organism in its untransformed state.

hPTH can then be used for all of its well known uses.

EXAMPLE 1

PRODUCTION OF HUMAN PTH(1–84)

*E. coli* transformed with pGFP-1 (see FIG. 2) in 10 ml were inoculated into a liter of LB ampicilline medium. When the culture reached an optical density of 600 nm, 40 mg. of 3β-indoleacrylic acid were added and the cultures induced for 16 hr. at 37° C. Cells were pelleted by centrifugation at 5000×g for 10 min, were resuspended in 100 ml of TE-sucrose to which 100 mg of lysozyme was added. After 1.5 hrs. incubation at 0° C., $MgCl_2$ was added to a concentration of 20 mM and DNaseI to 50 μg/ml for a further 1.5 hrs. The cells were lysed by addition of 200 ml of a solution containing 0.2M NaCl, 1% deoxycholic acid, 1.6% Nonidet P40, 20 mM Tris-HCl (pH 7.3), 2 mM EDTA, and 0.5 mM dithiothreitol (DTT), and incubation for 1.5 hrs at 0° C. The lysate was pelleted at 5000×g for 10 min. The pellet was washed 4 times with 0.5% Triton X-100, mM EDTA, and 0.5 mM DTT, and a pellet enriched in fusion protein was obtained by centrifugation.

The fusion protein pellet was dissolved in 50 ml 6M guanidine-HCL, 20 mM Tris-HCl, (pH 7.5), 0.5 mM DTT, and 1 mM EDTA, such that the fusion protein was at 1 mg/ml. The solution was dialyzed against 50 mM Tris-HCl (pH 7.8), 0.1M NaCl.

Activated Factor X was added at a ratio of 1 mg per 100 mg fusion protein and the mixture incubated for 2 hrs. at 37° C. The solution was then applied to an HPLC RPC-18 system, and was eluted with a linear 30–70% acetonitrile/H2O gradient. The PTH fraction was found to elute at 38% acetonitrile. The fraction was lyophilized and resuspended in water for subsequent analysis.

It was found that the GH-PTH fusion protein was hydrophobic and eluted at 68%a acetonitrile. Following treatment with Factor Xa, the hybrid protein peak was markedly diminished with the concomitant appearance of the PTH peak at 38% acetonitrile.

Yields of hybrid GH-PTH were generally about 50 mg/liter of culture. By SDS-polyacrylamide gel electraphoretic analysis, the above conditions of Factor X treatment resulted in 50% conversion of the fusion protein to hPTH(1–84) and the GH fragment.

EXAMPLE 2

ANALYSIS OF AMINO ACID COMPOSITION AND N-TERMINAL SEQUENCE OF RECOMBINANT HPTH(1–84)

Amino acid compositional analysis corresponded to the expected amino acid composition for hPTH(1–84). Gas phase microsequencing of the hPTH(1–84) confirmed the sequence for the first 18 amino acids. Significantly, N-terminal position 1 was found to be serine. There was no evidence of blocked amino termini in a significant portion of the hPTH produced, as has been described by others (Rabbani et al., 1988, supra).

EXAMPLE 3

BIOLOGICAL ACTIVITIES OF RECOMBINANT HPTH(1–84)

Figure 3A:
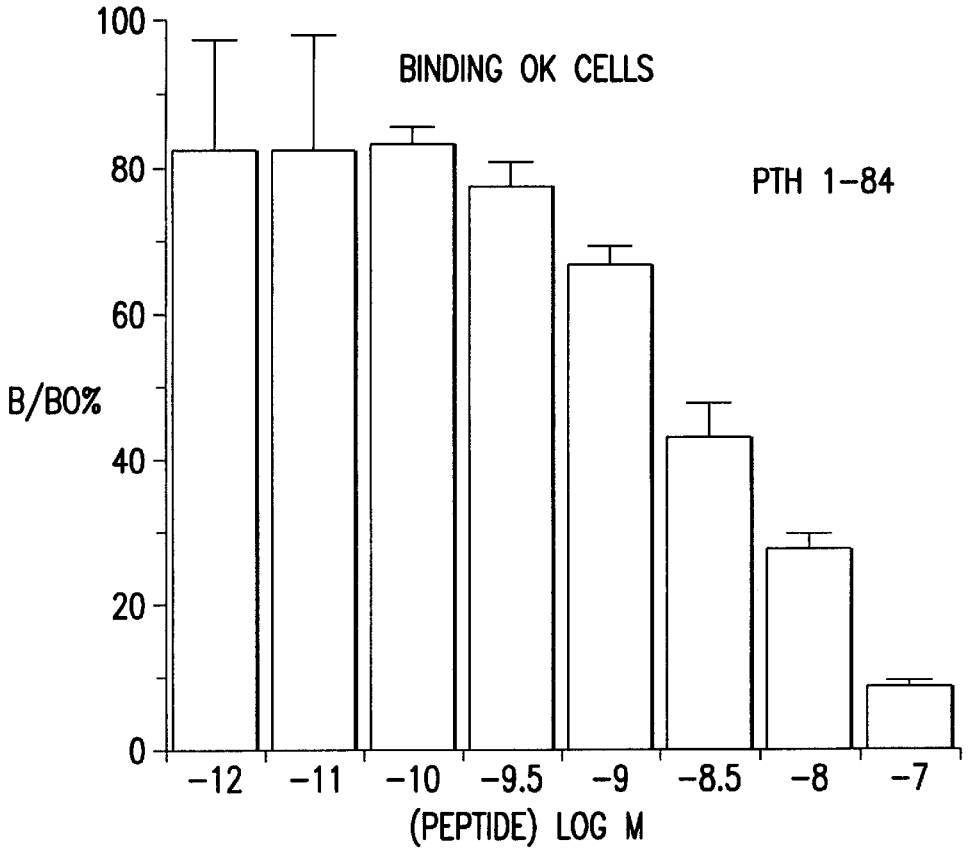
FIG. 3 shows binding of recombinant hPTH(1–84) and of synthetic PTH(1–34) to opossum kidney cells.
Figure 3B:
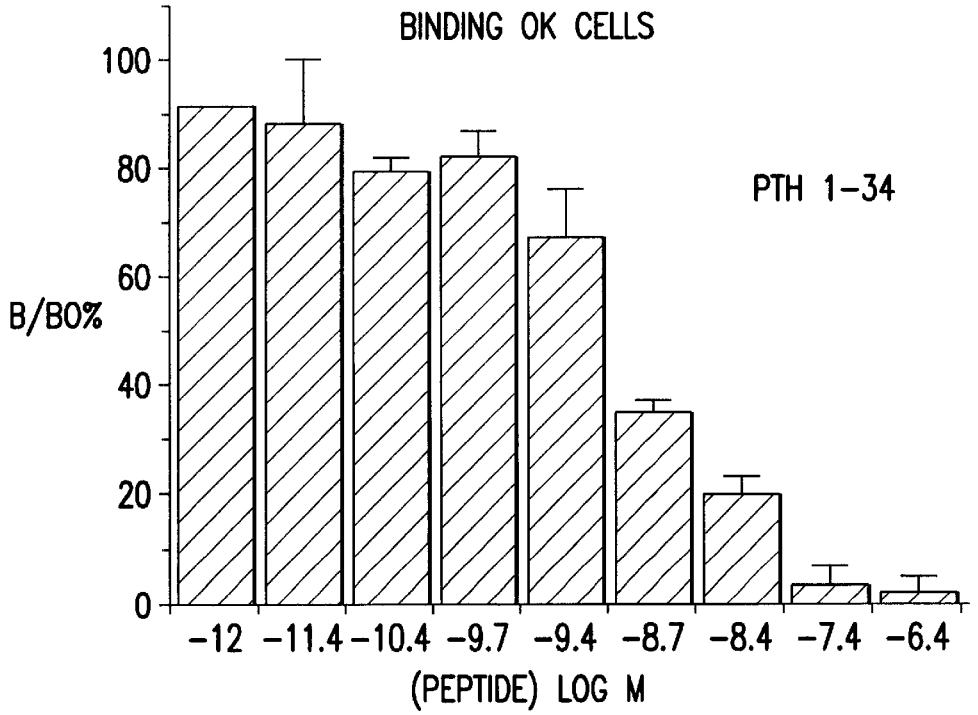
Figure 4A:
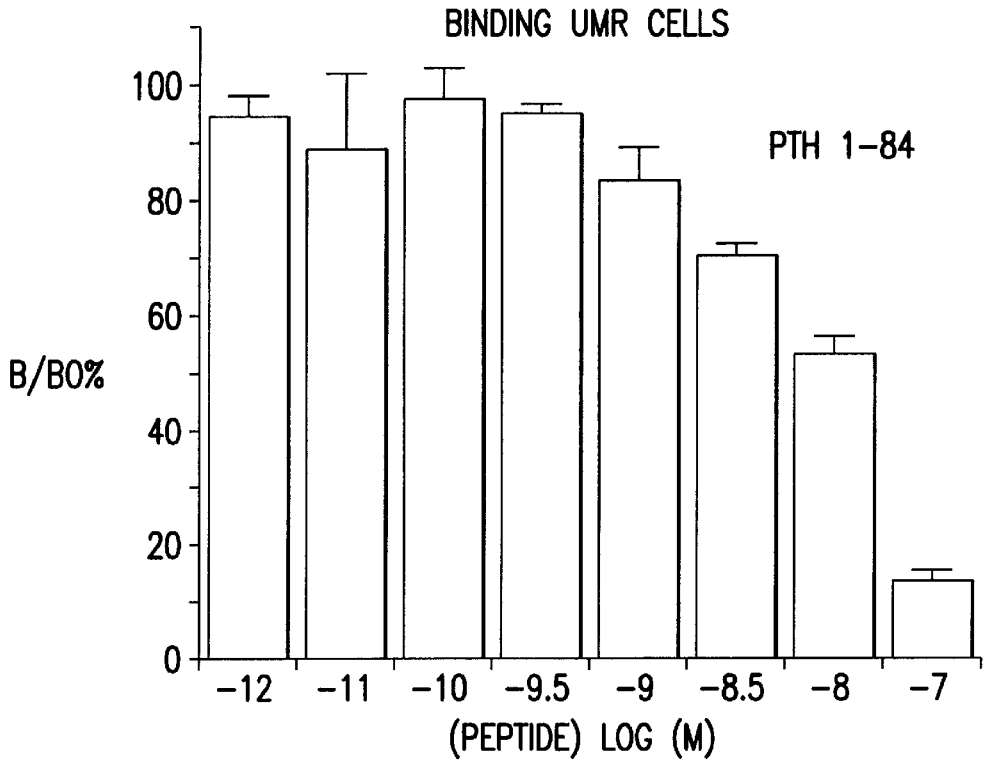
FIG. 4 shows binding of recombinant hPTH(1–84) and of synthetic PTH(1–34) to UMR tumor cells.
Figure 4B:
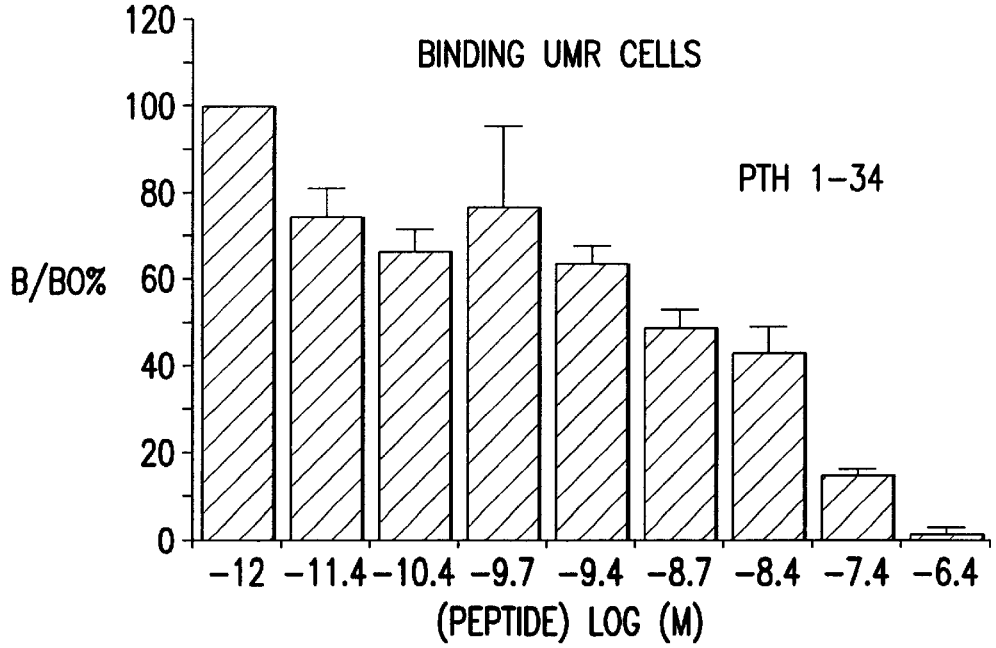

The recombinant peptide produced as described in Example 1 above was tested for it binding to two cells types. In FIG. 3 is shown data indicating that recombinant hPTH (1–84) bound specifically to opossum kidney cells, with half-maximal binding occurring at about 3 nM. This was similar to the binding of synthetic PTH(1–34) which demonstrated half-maximal binding at about 1 nM FIG. 4 depicts similar studies using the UMR rat osteosarcoma cell line, wherein the recombinant hPTH(1–84) bound with a half-maximum value of about 10 nM, compared to about 2 nM for synthetic PTH(1–34).

Figure 5A:
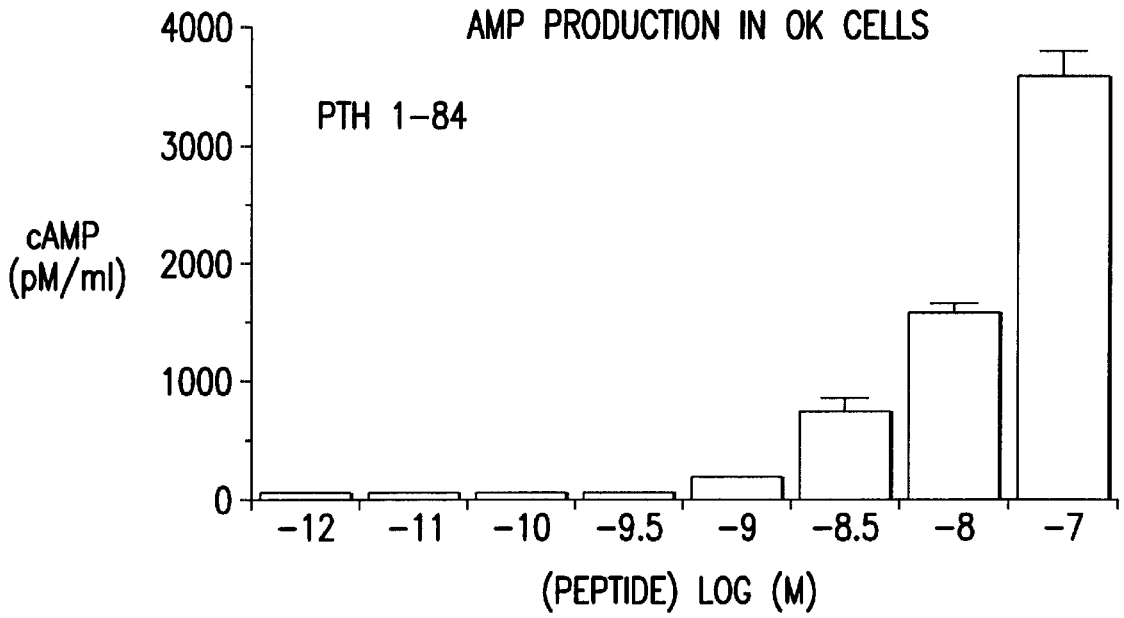
FIG. 5 shows the cyclic AMP response of opossum kidney cells to stimulation with recombinant hPTH(1–84) and synthetic PTH(1–34).
Figure 5B:
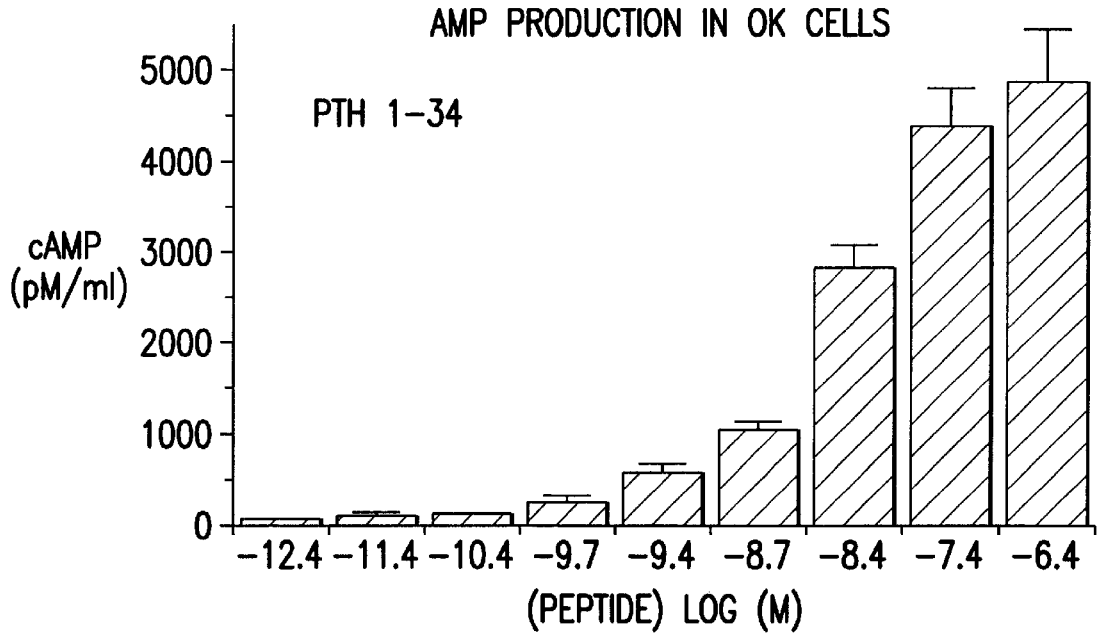
Figure 6A:
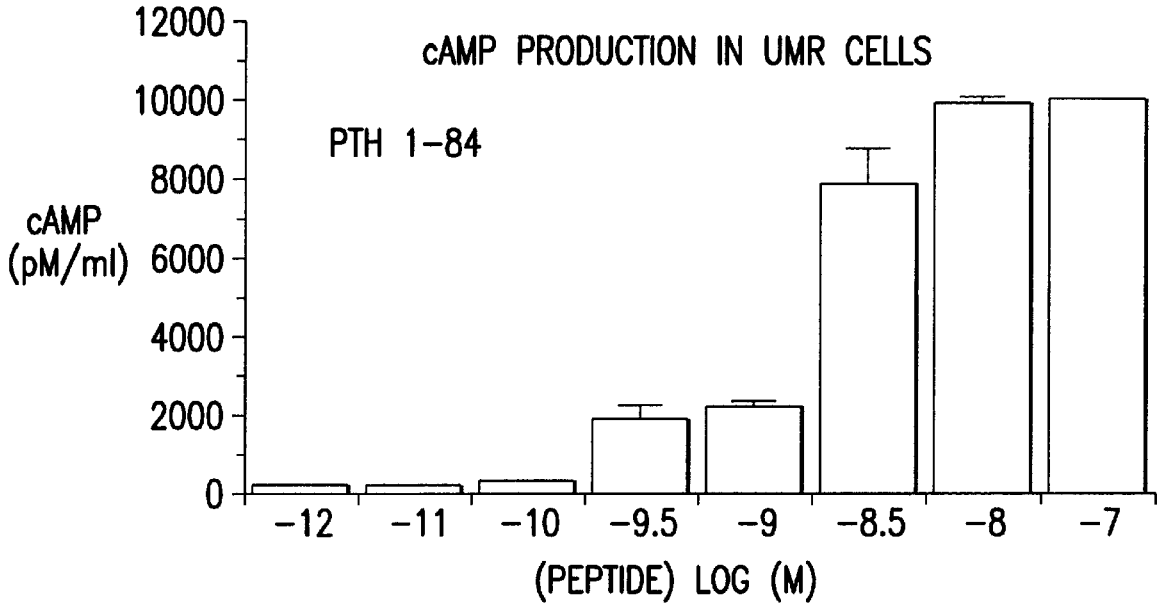
FIG. 6 shows the cyclic AMP response of UMR tumor cells to stimulation with recombinant hPTH(1–84) and synthetic PTH(1–34).
Figure 6B:
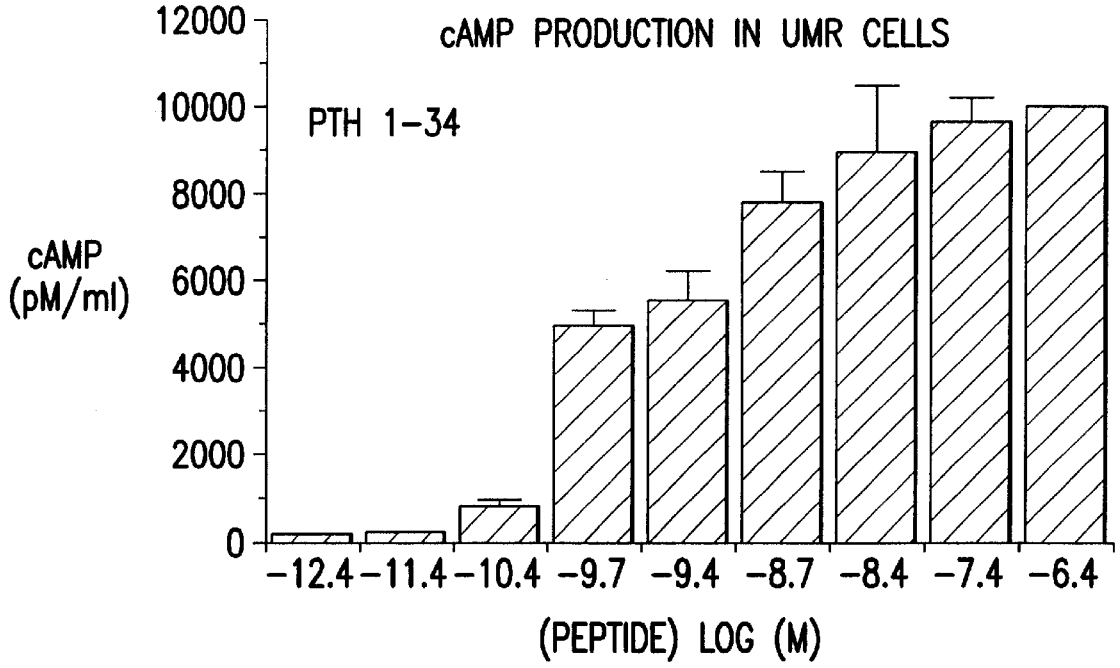

The biological activity of inducing cyclic AMP production is shown in FIGS. 5 and 6. Recombinant hPTH(1–84) stimulated cyclic AMP in opossum kidney cells with an $EC_{50}$ of about 10 nM, and synthetic PTH(1–34) had an $EC_{50}$ of about 4 nM (FIG. 5). In UMR cells recombinant hPTH (1–84) stimulated cyclic AMP with an $EC_{50}$ of about 3 nM, whereas synthetic PTH(1–34) had an $EC_{50}$ of about 0.1 nM (FIG. 6). Therefore, the recombinant peptide had PTH biological activity which is largely indistinguishable from that of a known active fragment.

DEPOSIT

*E. coli* strain DHl containing the plasmid pGFP-1 was deposited at the American Type Culture Collection, Rockville, MD, on May 12, 1989 and was given the accession number ATCC 67977.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A recombinant DNA molecule comprising:

(a) an expression control region, said region in operable linkage with:

(b) a leader sequence coding for human growth hormone amino acids 1–138 operably linked to:

(c) a nucleotide sequence coding for a selective enzymatic cleavage site, said nucleotide sequence being linked to and preceding a genetic sequence coding for human parathyroid hormone (hPTH) or a polypeptide variant thereof having the capacity to bind to a receptor for hPTH.

2. The molecule of claim 1 wherein said control region includes a bacterial, viral, fungal, or mammalian promoter.

3. The molecule of claim 2 wherein said promoter is selected from the group consisting of the right promoter of bacteriophage λ ($P_L$), the left promoter of bacteriophage λ ($P_R$), the *E. coli trp* promoter, the *E. coli recA* promoter, the *E. coli lacZ* promoter, the *E. coli lacI* promoter, the *E. coli gal* promoter, the *B. subtilis* α-amylase promoter, the *B. subtilis* α-28-specific promoter, the promoters of the bacteriophages of *Bacillus*, and the *Streptomyces* promoters.

4. The molecule of claim 3 wherein said promoter is the *E. coli trp* promoter.

5. The molecule of claim 1 wherein said selective enzymatic cleavage site is cleaved by Factor Xa.

6. The molecule of claim 5 wherein said selective enzymatic cleavage site is Ile-Glu-Gly-Arg.

7. The molecule of claim 1 wherein said selective enzymatic cleavage site is cleaved by thrombin.

8. The molecule of claim 1 wherein said selective enzymatic cleavage site is Leu-Val-Pro-Arg.

9. The molecule of claim 8 wherein said human parathyroid hormone is hPTH (1–84).

10. The molecule of claim 8 wherein said polypeptide variant thereof having the capacity to bind to a receptor for hPTH is truncated at the N-terminus.

11. The molecule of claim 10 wherein said polypeptide variant thereof having the capacity to bind to a receptor for hPTH is selected from the group consisting of hPTH(2–84), hPTH(3–84), hPTH(4–84), hPTH(5–84), hPTH(6–84), hPTH(7–84), and hPTH(8–84).

12. The recombinant DNA molecule of claim 1 which is a plasmid.

13. The plasmid of claim 12 which is pGFP-1.

14. A host cell containing the molecule of claim 1.

15. The cell of claim 14 which is prokaryotic.

16. The cell of claim 15 which is bacterial.

17. The cell of claim 16 which is of the species *E. coli.*

18. The cell of claim 14 which is eukaryotic.

19. The cell of claim 18 which is a yeast cell or a mammalian cell.

20. A method of producing human parathyroid hormone (hPTH) or a polypeptide variant thereof having the capacity to bind to a receptor for hPTH, substantially free of natural contaminants, comprising:

(a) providing the molecule of claim 7 in a host;

(b) expressing said human parathyroid hormone or a polypeptide variant thereof having the capacity to bind to a receptor for hPTH thereof; and (c) obtaining a fusion protein containing a human growth hormone, fused to a selective enzymatic cleavage site, fused to hPTH(1–84) or a polypeptide variant thereof having the capacity to bind to a receptor for hPTH; and (d) cleaving said fusion protein of step (c) with an enzyme recognizing said selective enzymatic cleavage site.

21. The method of claim 20 further comprising:

(f) purifying said hPTH(1–84) or said polypeptide variant thereof having the capacity to bind to a receptor for hPTH.

22. A fusion protein comprising:

(a) a human growth hormone 1–138 fused to (b) a selective enzymatic cleavage site, fused to (c) hPTH(1–84) or a polypeptide variant thereof having the capacity to bind to a receptor for hPTH.

23. The protein of claim 22 wherein said selective enzymatic cleavage site is cleaved by Factor Xa.

24. The protein of claim 22 wherein said selective enzymatic cleavage site is Ile-Glu-Gly-Arg.

25. The protein of claim 22 wherein said selective enzymatic cleavage site is cleaved by thrombin.

26. The protein of claim 22 wherein said selective enzymatic cleavage site is Leu-Val-Pro-Arg.

27. The protein of claim 22 wherein said polypeptide variant thereof having the capacity to bind to a receptor for hPTH is selected from the group consisting of hPTH(2–84), hPTH(3–84), hPTH(4–84), hPTH(5–84, hPTH(6–84), hPTH(7–84), and hPTH(8–84).

28. The protein of claim 27 wherein said polypeptide variant thereof having the capacity to bind to a receptor for hPTH is hPTH(3–84).

*29. The method of claim 21 wherein said hPTH(1–84) is purified using an HPLC RPC-18 system and is eluted with a linear 30–70% acetonitrile/$H_2O$ gradient.*

*30. Human parathyroid hormone substantially free of natural contaminants produced according to the method of claim 29.*

* * * * *